(12) United States Patent
Daaland et al.

(10) Patent No.: US 6,240,160 B1
(45) Date of Patent: May 29, 2001

(54) SYSTEM FOR INSPECTION OF PIPELINES

(75) Inventors: Alf Daaland, Melhus; Svein Åge Holen, Trondheim, both of (NO)

(73) Assignee: Den Norske Stats Oljeselskap A.S., Stavanger (NO)

( * ) Notice: Subject to any disclaimer, the term of this patent is extended or adjusted under 35 U.S.C. 154(b) by 0 days.

(21) Appl. No.: 09/269,052
(22) PCT Filed: Aug. 29, 1997
(86) PCT No.: PCT/NO97/00225
§ 371 Date: Jun. 14, 1999
§ 102(e) Date: Jun. 14, 1999
(87) PCT Pub. No.: WO98/12545
PCT Pub. Date: Mar. 26, 1998

(30) Foreign Application Priority Data

Sep. 19, 1996 (NO) ........................................ 963923

(51) Int. Cl.⁷ ...................................................... G01N 23/02
(52) U.S. Cl. ............................ 378/59; 378/60; 378/163; 378/205; 138/132
(58) Field of Search .............................. 378/59, 205, 206, 378/207, 58, 162, 60, 163, 62; 138/124, 132, 137, 138, 140

(56) References Cited

U.S. PATENT DOCUMENTS

| | | | |
|---|---|---|---|
| 3,836,776 | 9/1974 | Gullekson | 378/163 |
| 3,952,194 | 4/1976 | Bayonnet | 378/61 |
| 3,956,631 | 5/1976 | Crosby, Jr. | 378/58 |
| 4,006,359 * | 2/1977 | Sullins et al. | 378/60 |
| 4,187,423 | 2/1980 | Ehrhardt | 378/164 |
| 4,411,014 | 10/1983 | Berman | 378/59 |
| 4,862,808 * | 9/1989 | Hedgcoxe et al. | 378/60 |
| 5,864,601 * | 1/1999 | Cattorini et al. | 378/59 |

FOREIGN PATENT DOCUMENTS

| | | |
|---|---|---|
| 1319897 | 6/1973 | (GB) . |
| 1436960 | 5/1976 | (GB) . |
| 2143379 | 2/1985 | (GB) . |

OTHER PUBLICATIONS

Patent Abstracts of Japan, (JP 60–244843), vol. 10, No. 116, p. 452 (Dec. 4, 1985).
Patent Abstracts of Japan, (JP 2–291948), vol. 15, No. 71, p. 1168 (Dec. 3, 1990).

* cited by examiner

Primary Examiner—Robert H. Kim
Assistant Examiner—Drew A. Dunn
(74) Attorney, Agent, or Firm—Foley & Lardner

(57) ABSTRACT

A system for inspecting pipelines, especially in the coupling between pipe parts, comprises a radiation source and a detector device or a photographic film. The pipeline includes indicators which are laid into the pipeline material and have a differing absorption of radiation than the material comprising the layers of the pipeline in which the indicators are formed. By placing the radiation source and the detector device (or photographic film) on opposite sides of the pipeline, or on opposite sides of a wall of the pipeline, the position of the indicators may be detected, and any displacement can be measured.

22 Claims, 1 Drawing Sheet

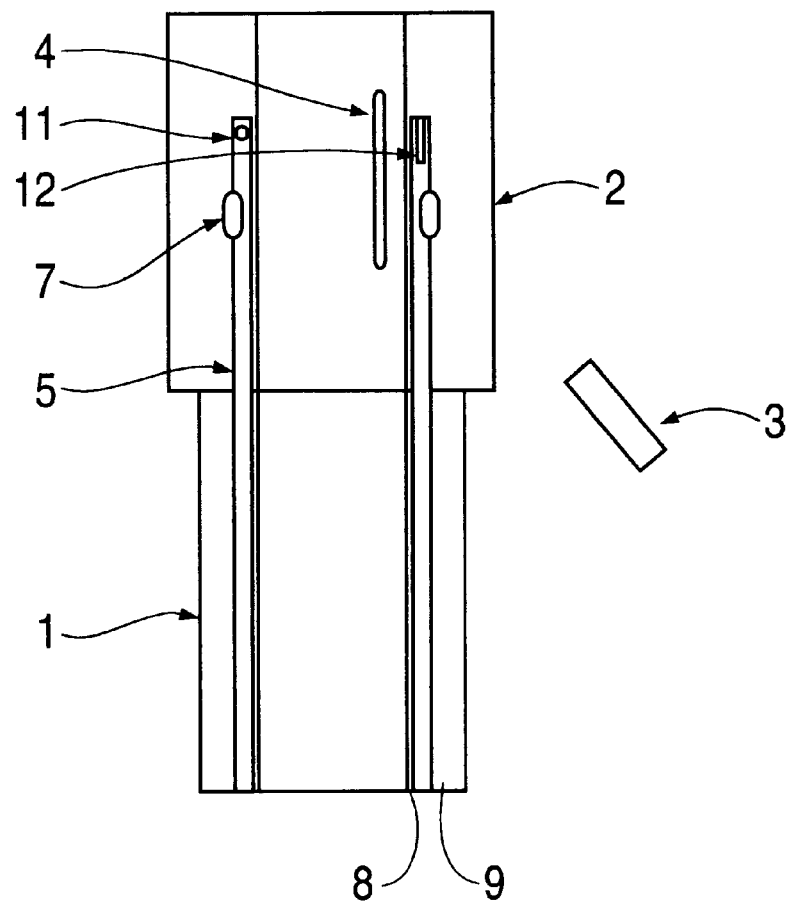
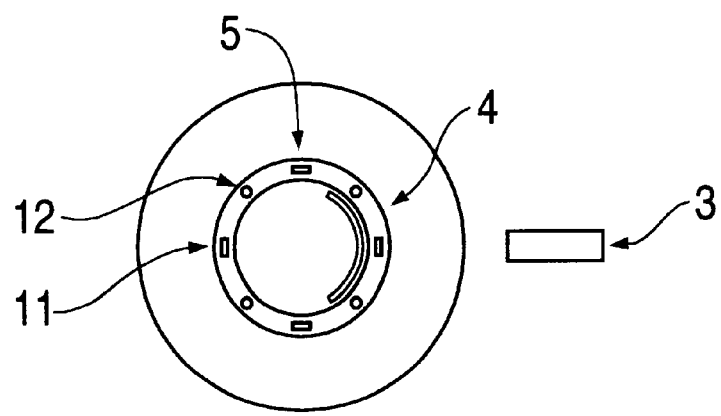

SYSTEM FOR INSPECTION OF PIPELINES

FIELD OF THE INVENTION

The invention relates to a system for inspection of pipelines, especially the coupling between parts of the pipe, comprising an x-ray source, a detector device for detection of x-rays, possibly a photographic film being sensitive in the x-ray range, adapted to receive the radiation and to be positioned on the opposite side of the pipe wall or pipeline in relation to the source.

BACKGROUND OF THE INVENTION

Pipelines being used in the oil and gas field are often subject to large strain in the form of stress, pressure and temperature variations. Because of this the pipelines are frequently inspected for displacements, cracks or possible leaks. A known method for performing such inspections is x-ray photographing of the pipeline. Different systems performing such inspections are available on the market.

Flexible pipelines are built to stand the abovementioned strains. A usual structure of flexible pipelines is a multi-layer system of steel pipes with polymer materials between them. The polymer layers include a pressure sheet which hinders diffusion and leakage of the pipeline content out into the environment. It is also demanded that the pressure sheet is able to move relatively freely in relation to the steel pipes, thus not to be subject to unnecessary strain when the pipeline moves. Between the pressure sheet and the steel pipes an anti-creep sheet is often placed in order to keep the pressure sheet from fastening to the steel layers. In the ends of each pipe part a coupling part is comprised which among other things may comprise a sealing or a packing ring providing a seal between the pipelines and also between the pressure sheets.

A problem relating to the abovementioned structure is that the pressure sheet has shown a tendency to contract and thus be drawn away from the sealing ring, making the pipeline leaky.

SUMMARY OF THE INVENTION

It is an object of the present invention to provide a system to be able to detect relative displacements between parts in a pipe system. It is especially preferred to provide a system being capable of detecting and measuring displacements in polymer layers or the like between steel layers in a pipeline, especially in the vicinity of the coupling points between the different pipe elements.

The present invention is a system for inspecting movable or deformable layers in pipelines, comprising an x-ray radiation source positioned on one side of a pipeline or a wall of the pipeline, a detector device or a photographic film adapted to receive radiation and positioned on the opposite side of the pipeline wall or the pipeline in relation to the radiation source. The pipeline comprises at least a first material layer and a second material layer and at least one movable or deformable third material layer positioned between the first and second material layers, the third material layer being softer than the first and second material layers. The third material layer includes indicators, the indicators having a differing absorption of radiation from the third material layer.

The invention may further be defined wherein the indicators have a length larger than their thickness or width.

Further, the indicators may comprise wires or strings of a fourth material, the wires or strings having a thickness approximately one third of the thickness of the third material layer.

The pipeline in the present system may include more than two material layers that are harder than the third material layer. The more than two layers are alternating and separated by different ones from a plurality of third material layers. At least two of the third material layers include indicators.

Further, the indicators in each of the third material layers may have a different shape.

Imaging of the pipeline in the present invention may be performed from a plurality of directions, and a tomographic picture of the pipeline may be made from this imaging.

The pipeline may comprise coupling points between two parts of the pipeline. The pipeline at each of the coupling points may comprise one or more sealing rings, the sealing rings including indicators.

Each third material layer of the present invention may comprise one or more layers of different materials, these layers of different materials forming pressure sheets or anti-creep sheets.

Another embodiment of the present invention is a pipe section comprising a first material layer, a second material layer and at least one movable or deformable third material layer. The third material layer is positioned between the first and second material layers and is softer than the first and second material layers. The third material layer includes indicators having a differing absorption of radiation from the third material layer.

Yet another embodiment of the present invention is a method for inspecting movable or deformable layers in pipelines. The method comprises the steps of positioning an x-ray radiation source on one side of a pipeline or a wall of the pipeline and detecting radiation on the opposite side of the pipeline wall or the pipeline in relation to an x-ray radiation source. The pipeline comprises at least a first material layer and a second material layer and at least one movable or deformable third material layer. The third material layer is positioned between the first and second material layers and is softer than the first and second material layers. The third material layer includes indicators having a differing absorption of radiation from the third material layer.

This way a simple system is obtained for inspecting pipelines being mainly based upon already available equipment, the implementation of which in new (and existing) pipe systems being easy and relatively cheap.

BRIEF DESCRIPTION OF THE DRAWINGS

The invention is described in detail below with reference to a preferred embodiment shown in the enclosed figures.

FIG. 1 shows a cross-section of the system for inspecting the end of a pipe, as seen from one side.

FIG. 2 shows a sketch of a system corresponding to the system shown in FIG. 1, as seen from above.

DETAILED DESCRIPTION OF THE PREFERRED EMBODIMENT

FIG. 1 and FIG. 2 illustrate an inspection of the pipe end 2 in a pipeline 1 comprising a polymer layer 5 being positioned between two steel layers 8,9. The pipe end also comprises a sealing or packing ring 7 for tight coupling to another pipe element. In the polymer layer 5 marks or indicators 11,12 are placed, being made from a material having a higher dampening than the rest of the material in the pipeline, e.g. platinum or tungsten. Preferably these reference points have a known position. In this way reference points in the polymer layer 5 are obtained which may be seen by x-ray photography of the pipe end 2, and which thus may indicate a displacement of the polymer layer in relation to the steel layers. Thus, it may be discovered if the pressure sheet shrinks and moves past the seal 7. Preferably there are structures in the steel layers 8,9, possibly provided for other purposes, e.g. recesses for the sealing ring, which may serve as reference points so that movements in the polymer layer in relation to the steel layers may be measured easily.

In a preferred embodiment of the invention the indicators/marks 11,12 have oblong shapes and are positioned with a chosen orientation in the polymer layer 5 so that its position may be determined more easily. In the figures the indicators are given axial 11 and tangential 12 orientations, respectively. Intermediate orientations may of course also be chosen. In certain cases a radial orientation may also be chosen, which will provide an improved possibility for detecting squeezing and deformations in the polymer layer.

The most simple way to produce the indicators 11,12 may be from strings or wires by cutting them in desired lengths. The thickness of the wires may be chosen depending on the dimensions of the pipeline and the thickness of the polymer layer, and may also depend on the relationship between the x-ray absorption of the indicators and of the pipeline. In a preferred embodiment the indicators have a thickness of approximately ⅓ of the thickness of the polymer layer. Used in the oil and gas related activities, the indicators are preferably made from a corrosion resistant material.

The polymer layer will, as mentioned above, often comprise more than one layer, usually with a pressure sheet hindering leaks and diffusion of the pipelines contents and an anti-creep sheet stopping the pressure sheet from sticking to the steel layer. The indicators may be placed in one or more of these layers.

The x-ray imaging of the pipeline may be performed by using different types of well-known equipment, e.g. based upon cobalt sources, linear accelerators or corresponding high energy sources, preferably in the range of MeV, but the requirements to the source will of course depend on the materials used in the pipeline.

To detect the radiation and provide a picture of the pipeline, suitable types of photographic film may be used. Electronic detectors and imaging devices may, however, also be used. Neither the choice of source nor the choice of imaging unit are important to the present invention other than the obvious choices relating to the materials in the pipeline, the desired intensity, etc, that need to be made in order to obtain a sufficiently sharp picture with sufficient contrast.

In the figures a method is illustrated in which a photographic film 4 is placed inside the pipe and the source 3 is outside the pipe. In an embodiment of the present invention several pictures are taken at different angles, which are combined electronically to, with available software, to provide a tomographic picture of the pipeline.

In another embodiment of the invention the source 3 and the film 4 or imaging device are positioned outside, and on either side, of the pipeline. Using tomographic techniques a complete picture of the pipeline and the possible displacements of the indicators may be obtained. This solution may also give an opportunity to inspect the pipeline in its full length, possibly without disassembling the pipeline. If this method for measuring is to be used, it may, under some circumstances, be topical to place the indicators along the whole length of the pipeline.

The figures show a simplified version of a pipeline. As mentioned above the pipeline 1 will comprise several types of polymer layers, pressure sheets and anti-creep sheets, and layers of steel or corresponding materials. The indicators in the different layers may be placed with varying positions or orientations depending on in which layer they are, or possibly with other, more complex shapes in order to provide a clearer view showing which layers are out of place. In such complex pipelines tomographic method may be utilized advantageously.

In another embodiment of the invention the system according to the invention may be used to control the position of the sealing or packing rings by laying the indicators 11,12 into it. If the pipeline comprises more than one sealing rings, the indicators may be placed in one or more of them.

In another embodiment of the invention the system according to the invention may also be utilized for inspecting pipelines that do not comprise several layers, e.g. simple plastic or steel pipes. In this case the indicators may be positioned directly in relation to the pipeline material, e.g. in order to measure displacements between two coupled parts of a pipeline.

The present invention may, as mentioned above, be used in relation to pipelines in oil or gas related activities, but is not limited to this. Different pipe materials, radioactive or x-ray sources, detectors or imaging methods, and indicator-materials may be chosen depending on the particular pipe system and the available equipment.

What is claimed is:

1. A system for inspecting movable or deformable layers in pipelines, comprising an X-ray radiation source positioned on one side of a pipeline or a wall of said pipeline, a detector device or a photographic film, adapted to receive radiation and positioned on the opposite side of said pipeline wall or said pipeline in relation to said X-ray radiation source, said pipeline comprising at least a first material layer and a second material layer and at least one movable or deformable third material layer positioned between said first and second material layers, said third material layer being softer than said first and second material layers, wherein said third material layer includes indicators, said indicators having a differing absorption of radiation from said third material layer.

2. A system according to claim 1, wherein said indicators have a length larger than their thickness or width.

3. A system according to claim 2, wherein said indicators comprise wires or strings of a fourth material, said wires or strings having a thickness approximately one third of the thickness of said third material layer.

4. A system according to claim 2, wherein the orientation of each of the indicators, when photographed with the radiation source, allows determination of the position of the photographed structures.

5. A system according to claim 1, wherein the pipeline includes more than two material layers that are harder than said third material layer, said more than two material layers alternating and being separated by different ones from a plurality of third material layers, and wherein at least two of said third material layers include indicators.

6. A system according to claim 5 wherein the indicators in each of said third material layers has a different shape.

7. A system according to claim 1,
wherein imaging of the pipeline is performed from a plurality of directions, and a tomographic picture of the pipeline is made from this imaging.

8. A system according to claim 1,
wherein the pipeline comprises coupling points between two parts of the pipeline, the pipeline at each of said coupling points comprising one or more sealing rings, said sealing rings including indicators.

9. A system according to claim 1,
wherein each third material layer comprises one or more layers of different materials, said layers of different materials forming pressure sheets or anti-creep sheets.

10. A system according to claim 1,
wherein the pipeline comprises a number of interconnected pipes, and said indicators are positioned close to the ends of the pipes.

11. A system according to claim 1,
wherein the indicators are made from a corrosion resistant material.

12. A system according to claim 5,
wherein imaging of the pipeline is performed from a plurality of directions, and a tomographic picture of the pipeline is made from this imaging.

13. A system according to claim 5,
wherein the pipeline comprises coupling points between two parts of the pipeline, the pipeline at each of said coupling points comprising one or more sealing rings, said sealing rings including indicators.

14. A system according to claim 5,
wherein each third material layer comprises one or more layers of different materials, said layers of different materials forming pressure sheets or anti-creep sheets.

15. A system according to claim 5,
wherein the pipeline comprises a number of interconnected pipes, and said indicators are positioned close to the ends of the pipes.

16. A system according to claim 5,
wherein the indicators are made from a corrosion resistant material.

17. A pipe section comprising:
a first material layer;
a second material layer; and
at least one movable or deformable third material layer positioned between said first and second material layers, said third material layer being softer than said first and second material layers and including indicators having a differing absorption of X-ray radiation from said third material layer.

18. The pipe section according to claim 17, further comprising:
at least one additional movable or deformable third material layer; and
at least one additional material layer that is harder than said third material layer,
wherein said first, second and additional harder material layers alternate with and are separated by different ones from the plurality of said third material layers, and at least two of said third material layers include indicators.

19. The pipe section according to claim 17,
further comprising coupling points on at least one end of pipe section, the pipe section at the coupling point comprising one or more sealing rings, said sealing rings including indicators.

20. The pipe section according to claim 17,
wherein each third material layer comprises one or more layers of different materials, said layers of different materials forming pressure sheets or anti-creep sheets.

21. A method for inspecting movable or deformable layers in pipelines, comprising the steps of:
positioning an X-ray radiation source on one side of a pipeline or a wall of said pipeline; and
detecting radiation on the opposite side of said pipeline wall or said pipeline in relation to said X-ray radiation source;
wherein said pipeline comprises at least a first material layer and a second material layer and at least one movable or deformable third material layer positioned between said first and second material layers, said third material layer being softer than said first and second material layers; and
wherein said third material layer includes indicators, said indicators having a differing absorption of radiation from said third material layer.

22. The method as defied in claim 21, wherein said positioning and detecting steps further include the steps of positioning an X-ray radiation source and detecting the radiation therefrom in a plurality of different directions.

* * * * *